US006303653B1

(12) United States Patent
Bar-Tana (10) Patent No.: US 6,303,653 B1
(45) Date of Patent: Oct. 16, 2001

(54) CARBOXYLIC ACIDS AND DERIVATIVES THEREOF AND PHARMACEUTICAL COMPOSITIONS CONTAINING THEM

(75) Inventor: Jacob Bar-Tana, Jerusalem (IL)

(73) Assignee: Yissum Research Development Company of The Hebrew University of Jerusalem (IL)

( * ) Notice: Subject to any disclaimer, the term of this patent is extended or adjusted under 35 U.S.C. 154(b) by 0 days.

(21) Appl. No.: 09/104,880

(22) Filed: Jun. 25, 1998

(30) Foreign Application Priority Data

Jun. 26, 1997 (IL) ........................................ 121165

(51) Int. Cl.[7] ..................... A61K 31/255; A61K 47/00; A61K 31/275; C07C 61/00; C07K 16/00

(52) U.S. Cl. ......................... 514/527; 514/529; 514/784; 514/785; 514/824; 514/825; 514/903; 530/387.1; 562/400

(58) Field of Search .................................... 514/527, 529, 514/784, 785, 825, 824, 903; 530/387.1; 562/400

(56) References Cited

U.S. PATENT DOCUMENTS

| 4,634,795 | 1/1987 | Bar-Tana | 562/590 |
|---|---|---|---|
| 4,689,344 | 8/1987 | Bar-Tana | 514/527 |
| 4,711,896 | 12/1987 | Bar-Tana et al. | 514/570 |
| 5,641,810 | 6/1997 | Pill et al. | 514/558 |

FOREIGN PATENT DOCUMENTS

| 119971 | 1/1997 | (IL) . |
| 121165 | 6/1997 | (IL) . |
| WO 98/30530 | 7/1998 | (WO) . |

OTHER PUBLICATIONS

Bar–Tana et al., "Inhibition of lipid synthesis by β,β' tetramethyl–substituted C14–C22 α,ω dicarboxylic acids in the rat in vivo", *J. Biol. Chem.*, 260:8404–8410 (1985).

Bar–Tana et al., "Synthesis, hypolipidemic and antidiabetogenic activities of β,β'-tetra–substituted, long chain dioic acids", *J. Med. Chem.*, 32:2072–2084 (1989).

Bar–Tana, J., "Long chain dicarboxylic acids: Hypolipidemic, antiobesity and antidiabetic activity", In *New Antidiabetic Drugs*, (eds. Bailey CJ, Flatt PR), Smity–Tordon and Comp. (1990).

Bar–Tana et al., "The hypolipidemic effect of β,β'-methyl–substituted hexadecanedioic acid in normal and nephrotic rats", *J. Lipid Res.*, 29:4431–441 (1988).

(List continued on next page.)

Primary Examiner—Gary Geist
Assistant Examiner—Everett White
(74) Attorney, Agent, or Firm—Heller Ehrman White & McAuliffe LLP (57) ABSTRACT

In accordance with the present invention, there are provided therapeutically effective compounds comprising an amphipathic carboxylate of the formula R—COOH, or a salt or an ester or amide of such compound, where R designates a saturated or unsaturated alkyl chain of 10–24 carbon atoms, one or more of which may be replaced by heteroatoms, where one or more of said carbon or heteroatom chain members optionally forms part of a ring, and where said chain is optionally substituted by a hydrocarbyl radical, heterocyclyl radical, lower alkoxy, hydroxyl-substituted lower alkyl, hydroxyl, carboxyl, halogen, phenyl or (hydroxy-, lower alkyl-, lower alkoxy-, lower alkenyl- or lower alkinyl)-substituted phenyl, $C_3$–$C_7$ cycloalkyl or (hydroxy-, lower alkyl-, lower alkoxy-, lower alkenyl- or lower alkinyl)-substituted $C_3$–$C_7$ cycloalkyl wherein said amphipathic carboxylate is capable of being endogenously converted to its respective coenzyme A thioester.

8 Claims, 6 Drawing Sheets

OTHER PUBLICATIONS

DeFronzo et al., "Insulin resistance: a multifaceted syndrome responsible for NIDDM, obesity, hypertension, dyslipidemia and atherosclerotic cardiovascular disease", *Diabetes Care*, vol. 14, No. 3, 173–194 (1991).

Frenkel et al., "The hypochylomicronemic effect of β,β'–methyl–substituted hexadecanedioic acid is mediated by a decrease in apolipoprotein C–III", *J. Biol. Chem.*, 263:8491–8497 (1988).

Frenkel et al., "The effect of β,β'–methyl–substituted hexadecanedioic acid on plasma VLDL metabolism in rats: role of apolipoprotein C–IIL", *Biochem. J.*, 298:409–414 (1994).

Hermesh et al., "Mitochondria uncoupling by a long chain fatty acyl analogue", *J. Biol. Chem.*, In Press (1997). vol. 273, No. 7, Issue Feb. 13, 1998, pp. 3937–3942.

Hertz et al., "Mode of action of peroxisome proliferators as hypolipidemic drugs: suppression of apolipoprotein C–ILL", *J. Biol. Chem.*, 270:13470–13475 (1995).

Kahn–Rose et al., "Inhibition of lipid synthesis by β,β' tetramethyl–substituted $C_{14}$–$C_{22}$ α,ω dicarboxylic acids in cultured rat hepatocytes", *J. Biol. Chem.*, 260:8411–8415 (1985).

Kalderon et al., "Tissue selective modulation of redox and phosphate potentials by β,β'–methyl–substituted hexadecanedioic acid", *Endocrinology*, 131:1629–1635 (1992).

Mayorek et al., "Hypocholesterolemic effect of β,β'–methyl–substituted hexadecanedioic acid in the male hamster", *Biochem. J.*, 289:911–917 (1993).

Mayorek et al., "Sensitization to insulin induced by β,β'–methyl–substituted hexadecanedioic acid (MEDICA 16) in obese Zucker rats in vivo", *Diabetes*, (1997).

Russel et al., "The hypolipidemic effect of β,β' tetramethylhexadecanedioic acid (MEDICA 16) in hyperlipidemic JCR:LA–corpulent rats", *Arteriosclerosis and Thrombosis*, 11:602–609 (1991).

Russell et al., "Inhibition of atherosclerosis and myocardial lesions in the JCR:LA–cp rat by β,β'–tetramethyl hexadecanedioic acid", *Arterioscler. Thromb. Vasc. Biol.*, 15:918–923 (1995).

Tzur et al., "The hypolipidemic antiobesity and hypoglycemic–hypoinsulinemic effects of β,β'–methyl–substituted hexadecanedioic acid in sand rats", *Diabetes*, 37:1618–1624 (1988).

Tzur et al., "Adipose reduction by β,β'–tetramethyl–substituted hexadecanedioic acid (MEDICA 16)", *Int. J. Obesity*, 13:313–326 (1989).

Liimatta et al., "dietary polyunsaturated fatty Acids Interfere with the Insulin/Glucose Activation of I–Type Pyruvate Kinase Gene Transcription", Molecular Endocrinology, vol. 8, No. 9, Isued Sep. 1994, pp. 1147–1153, Sep. 1994.*

* cited by examiner

CARBOXYLIC ACIDS AND DERIVATIVES THEREOF AND PHARMACEUTICAL COMPOSITIONS CONTAINING THEM

FIELD OF THE INVENTION

The present invention relates to therapeutically effective compounds and methods of treating certain diseases/syndromes using such compounds.

REFERENCES

The following references are cited in the application as numbers in brackets or superscript at the relevant portion of the application.
1. Sladek, F. M., Zhong, W. M., Lai, E. Darnell, J. E., Jr. Gene Dev. 4, 2353–2365 (1990)
2. Sladek, F. M., in Liver Gene Expression (eds. Tronche, F. & Yaniv, M.) pp. 207–230, R. G. Landes Co., Austin, Tex. (1994)
3. The Metabolic and Inherited Bases of Inherited Disease (eds., Scriver, C. R., Beaudet, A. L., Sly, W. S., Valle, D.) Vol. II, Part 8, 1995 (McGraw-Hill, Inc.)
4. Yamagata, K. et al., Nature 384, 4588–60 (1996)
5. DeFronzo, R. A. & Eleaterio, F. Diabetes Care 14, 173–194(1991)
6. Leff, T., Reue, K., Melian, A., Culver, H. & Breslow J. L. J. Biol. Chem. 264, 16132–16137 (1989)
7. Cave, W. T. FASEB J. 5,2160–2166 (1991)
8. Chin, J. P. F. Prost. Leuk. Essent. Fatty Acids 50, 211–222 (1994)
9. Grundy, S. M. & Denke, M. A. J. Lipid Res. 31, 1149–1172 (1990)
10. Storlien, L. H. et al., Science 237, 885–888 (1987)
11. Unger, R. H. Diabetes 44, 863–870 (1995)
12. Morris, M. C., Saks, F. & Rosner, B. Circulation 88, 523–533 (1993)
13. Hultin, M. B. Prog. Hemost. Thromb. 10, 215–241 (1991)
14. Bar-Tana, J., Rose-Kahn, G., Frenkel, B., Shafer, Z. & Fainaru, M. J. Lipid Res. 29, 431–441 (1988)
15. Tzur, R., Rose-Kahn, G., Adler, J. & Bar-Tana, J. Diabetes 37, 1618–1624 (1988)
16. Tzur, R., Smith, E. & Bar-Tana, J. Int. J. Obesity 13, 313–326 (1989)
17. Russel, J. C., Amy, R. M., Graham, S. E., Dolphin, P. J. & Bar-Tana, J. Arterioscler.
Thromb. Biol. 15, 918–923 (1995)

The disclosure of the above publications, patents and patent applications are herein incorporated by reference in their entirety to the same extent as if the language of each individual publication, patent and patent application were specifically and individually included herein.

BACKGROUND

Hepatocyte nuclear factor-4α[1] (HNF-4, preferably HNF-4α, (reviewed in ref. 2) is an orphan member of the superfamily of nuclear receptors. HNF-4α is expressed in the adult and embryonic liver, kidney, intestine and pancreas and disruption of the murine HNF-4α by homologous recombination results in embryo death. Like other members of the superfamily, the HNF-4α receptor consists of a modular structure comprising a well conserved N-terminal DNA binding domain linked through a hinge region to a hydrophobic C-terminal ligand binding domain. Two HNF-4α isoforms have been cloned and characterized: HNF-4α1 and HNF-4α2 comprising of a splice variant having a 10 amino acids insert in the C-terminal domain.

HNF-4α is an activator of gene expression. Transcriptional activation by HNF-4α is mediated by its binding as a homodimer to responsive DR-1 promoter sequences of target genes resulting in activation of the transcriptional initiation complex. Genes activated by HNF-4α (reviewed in ref. 2) encode various enzymes and proteins involved in lipoproteins, cholesterol and triglycerides metabolism (apolipoproteins AI, AII, AIV, B, CIII, microsomal triglyceride transfer protein, cholesterol 7(hydroxylase), lipid metabolism (mitochondrial medium chain fatty acyl-CoA dehydrogenase, peroxisomal fatty acyl-CoA oxidase, cytochrome P-450 isozymes involved in fatty acyl ω-oxidation and steroid hydroxylation, fatty acid binding protein, cellular retinol binding protein II, transthyretin), glucose metabolism (phosphoenolpyruvate carboxykinase, pyruvate kinase, aldolase, glut2), amino acid metabolism (tyrosine amino transferase, ornitine transcarbamylase), blood coagulation (factors VII, IX, X), iron metabolism (transferrin, erythropoietin) and macrophage activation (hepatocyte growth factor-like protein/macrophage stimulating protein, Hepatitis B core and X proteins, long terminal repeat of human HIV-1, α-1 antitrypsin).

Some genes activated by HNF-4α play a dominant role in the onset and progression of atherogenesis, cancer, autoimmune and some other diseases[3]. Thus, overexpression of apolipoproteins B, AIV and CIII as well as of microsomal triglyceride transfer protein may result in dyslipoproteinemia (combined hypertriglyceridemia and hypercholesterolemia) due to increased production of very low density lipoproteins (VLDL) and chylomicrons combined with decrease in their plasma clearance. Similarly, enhanced pancreatic glycolytic rates leading to HNF-4α/HNF-1-induced overexpression/oversecretion of pancreatic insulin may result in hyperinsulinemia leading to insulin resistance. Indeed, mutations in HNF-4α and HNF-1 were recently shown to account for maturity onset diabetes of the young (MODY)[4]. Insulin resistance combined with HNF-4α-induced overexpression of liver phosphoenolpyruvate carboxykinase and increased hepatic glucose production may result in impaired glucose tolerance (IGT) leading eventually to noninsulin dependent diabetes mellitus (NIDDM). Furthermore, hyperinsulinemia is realized today as major etiological factor in the onset and progression of essential hypertension and overexpression of HNF-4α controlled genes may therefore further lead to hypertension. Furthermore, HNF-4α-induced overexpression of blood coagulation factors combined perhaps with overexpression of inhibitors of blood fibrinolysis (e.g., plasminogen activator inhibitor-1) may lead to increased thrombus formation and decreased fibrinolysis with a concomitant aggravation of atherosclerotic prone processes.

Dyslipoproteinemia, obesity, IGT/NIDDM, hypertension and coagulation/fibrinolysis defects have been recently realized to be linked by a unifying Syndrome (Syndrome-X, Metabolic Syndrome, Syndrome of insulin resistance)[5]. High transcriptional activity of HNF-4α resulting in overexpression of HNF-4α-controlled genes may indeed account for the etiological linkage of Syndrome-X categories. Syndrome-X categories and the Syndrome in toto are realized today as major risk factors for atherosclerotic cardiovascular disease in Western societies, thus implicating HNF-4α in initiating and promoting atherogenesis. Furthermore, since breast, colon and prostate cancers are initiated and promoted in Syndrome-X inflicted individuals, overexpression of HNF-4α controlled genes could be implicated in the onset and progression of these malignancies.

In addition to the role played by HNF-4α in the expression of Syndrome-X related genes, HNF-4α activates the expression of genes which encode for proteins involved in modulating the course of autoimmune reactions. Thus, HNF-4α-induced overexpression of the macrophage stimulating protein may result in sensitization of macrophages to self antigens or crossreacting antigens, thus initiating and exacerbating the course of autoimmune diseases, e.g., rheumatoid arthritis, multiple sclerosis and psoriasis. Furthermore, since transcription of hepatitis B core and X proteins as well as the long terminal repeat of human HIV-1 are controlled by HNF-4α, HNF-4α could be involved in modulating the course of infection initiated by these viral agents.

Since overexpression of HNF-4α-induced genes may result in dyslipoproteinemia, IGT/NIDDM, hypertension, blood coagulability and fibrinolytic defects, atherogenesis, cancer, inflammatory, immunodeficiency and other diseases, inhibition of HNF-4α transcriptional activity may be expected to result in amelioration of HNF-4α-induced pathologies. However, no ligand has yet been identified for HNF-4α which could serve as basis for designing inhibitors of HNF-4α transcriptional activity. This invention is concerned with low molecular weight ligands of HNF-4α designed to act as modulators of HNF-4α-induced transcription and therefore as potential drugs in the treatment of pathologies induced by or involving HNF-4α-controlled genes.

SUMMARY OF THE INVENTION

In accordance with the present invention, there are provided therapeutically effective compounds comprising an amphipathic carboxylate of the formula R—COOH, or a salt or an ester or amide of such compound, where R designates a saturated or unsaturated alkyl chain of 10–24 carbon atoms, one or more of which may be replaced by heteroatoms, where one or more of said carbon or heteroatom chain members optionally forms part of a ring, and where said chain is optionally substituted by a hydrocarbyl radical, heterocyclyl radical, lower alkoxy, hydroxyl-substituted lower alkyl, hydroxyl, carboxyl, halogen, phenyl or (hydroxy-, lower alkyl-, lower alkoxy-, lower alkenyl- or lower alkinyl)-substituted phenyl, $C_3$–$C_7$ cycloalkyl or (hydroxy-, lower alkyl-, lower alkoxy-, lower alkenyl- or lower alkinyl)-substituted $C_3$–$C_7$ cycloalkyl wherein said amphipathic carboxylate is capable of being endogenously converted to its respective coenzyme A thioester.

In a preferred embodiment the amphipathic carboxylate is a xenobiotic amphipathic carboxylate. In a more preferred embodiment, the xenobiotic amphipathic carboxylate may be a long chain dicarboxylic acid, α-OH carboxylic acid, α-B(OH)$_2$ carboxylic acid, an analogue of clofibric acid or a nonsteroidal antiinflammatory drug. In a most preferred embodiment the amphipathic carboxylated is selected from the group consisting of Stearoyl(18:0)-CoA, Oleoyl(18:1)-CoA, Linolenoyl(18:2)-CoA, Linolenoyl(18:3)-CoA, Eicosa-pentaenoyl(20:5)-CoA, Docosahexaenoyl(22:6)-CoA, 1,16 Hexadecanedioic acid, 1,18 Octadecanedioic acid 2,2,15,15-tetramethylhexadecane-1,16-dioic acid, 2,2,17,17-tetramethylocta-decane-1,18-dioic acid, 3,3,14,14-tetramethyl-hexadecane-1,16-dioic acid, 3,3,16,16-tetramethyl-octadecane-1,18-dioic acid, 4,4,13,13-tetramethyl-hexadecane-1,16-dioic acid, 4,4,15,15-tetramethyl-octadecane-1,18-dioic acid, 16-B(OH)2-hexadecanoic acid, 18-B(OH)2-octadecanoic acid, 16-B(OH)2–2,2-dimethyl-hexadecanoic acid, 18-B(OH)2-2,2-dimethyl-octadecanoic acid, 16-B(OH)2-3,3-dimethyl-hexadecanoic acid, 18-B(OH)2–3,3-dimethyl-octadecanoic acid, 16-B(OH)2-4 4,4-dimethyl-hexadecanoic acid, 18-B(OH)2-4,4-dimethyl-octadecanoic acid, 16-hydroxy-hexadecanoic acid, 18-hydroxy-octadecanoic acid, 16-hydroxy-2,2-dimethyl-hexadecanoic acid, 18-hydroxy-2,2-dimethyl-octadecanoic acid, 16-hydroxy-3,3-dimethyl-hexadecanoic acid, 18-hydroxy-3,3-dimethyl-octadecanoic acid, 16-hydroxy-4,4-dimethyl-hexadecanoic acid, and 18-hydroxy-4,4-dimethyl-octadecanoic acid.

In another aspect of the present invention there is provided a method of treatment for Syndrome X comprising administering a therapeutically effective amount of an amphipathic carboxylate. In a preferred embodiment each of the diseases comprising Syndrome X may be treated individually.

In another aspect of the present invention, there are provided methods of modulating HNF-4α activity.

In yet another aspect, there are provided methods of treating a disease or syndrome comprising the administration of a therapeutically effective amount of an amphipathic carboxylate. Diseases such as, for example, breast cancer, colon cancer and prostate cancer may be treated using the inventive methods.

BRIEF DESCRIPTION OF THE DRAWINGS

FIG. 1 shows that long chain acyl-CoAs are ligands for HNF-4I. The GST-HNF-4I(LBD) fusion protein (I) consists of HNF-4I(LBD) fused to glutathione-S transferase. The His-HNF-4I (n) consists of the full length HNF-4I tagged by 6 histidines.

a. Saturation binding curve for palmitoyl(16:0)-CoA. The respective recombinant proteins are incubated to equilibrium with [$^3$H]palmitoyl(16:0)-CoA (0.05 μCi) and with increasing nonlabeled palmitoyl(16:0)-CoA as indicated. A dissociation constant (Kd) of 2.6 μM and maximal binding of 1 mol palmitoyl(16:0)-CoA/mol HNF-4I are determined by Scatchard analysis.

b. Competition by myristoyl(14:0)-CoA. The respective recombinant proteins are incubated with 8 nM of [$^3$H] palmitoyl(16:0)-CoA (60 Ci/mmol) and with increasing nonlabeled myristoyl(14:0)-CoA as indicated. Percent bound refers to radiolabeled [$^3$H]palmitoyl(16:0)-CoA in the bound fraction. 100% binding amounts to 0.3 pmol of [$^3$H]palmitoyl(16:0)-CoA. Percent bound refers to radiolabeled [$^3$H]palmitoyl(16:0)-CoA in the bound fraction. 100% binding amounts to 0.3 pmol of [$^3$H]palmitoyl(16:0)-CoA. $EC_{50}$ (50% specific competition) amounts to 1.4 μM (range 1.2–1.5 μM) of myristoyl(14:0)-CoA. $EC_{50}$ for other fatty acyl-CoAs and xenobiotic acyl-CoAs are as follows:

| | | |
|---|---|---|
| Dodecanoyl(12:0)-CoA | 2.3 μM | (range 2.1–2.4 μM); |
| Palmitoyl(16:0)-CoA | 2.6 μM | (range 1.3–3.4 μM); |
| Stearoyl(18:0)-CoA | 2.7 μM | (range 2.1–3.3 μM); |
| Oleoyl(18:1)-CoA | 1.4 μM | (range 1.0–1.8 μM); |
| Linoleoyl(18:2)-CoA | 1.9 μM | (range 1.5–2.3 μM); |
| Linolenoyl(18:3)-CoA | 2.9 μM | (range 2.9–3.8 μM); |
| Eicosapentaenoyl(20:5)-CoA | 0.6 μM | (range 0.5–0.7 μM); |
| Docosahexaenoyl(22:6)-CoA | 1.6 μM | (range 0.6–2.7 μM). |
| 3,3,16,16-tetramethyl-octadecanedioic acid | 8 μM | (range 5–15 μM) |
| 3,3,14,14-tetramethyl-hexadecanedioic acid | 8 μM | (range 5–15 μM) |
| 3,3,12,12-tetramethyl-tetradecanedioic acid | 40 μM | |
| Bezafibrate | 90 μM | |
| Nafenopin | 90 μM | |
| Ibuprofen | 40 μM | |

FIG. 2 shows that fatty acyl-CoA ligands of HNF-4α modulate its binding to its cognate DNA enhancer.

a. His-HNF-4I (14 ng) binding to C3P in the absence (lane 1) or presence of 10 µM each of myristoyl(14:0)-CoA (lane 2) or palmitoyl(16:0)-CoA (lane 3).

b. His-HNF-4I (20 ng) binding to C3P in the absence (lane 1) or presence of 10 µM each of stearoyl(18:0)-CoA (lane 2) or linolenoyl(18:3, w-3)-CoA (lane 3).

c. Activation of His-HNF-4I (14 ng) binding to C3P by increasing concentrations of myristoyl(14:0)-CoA. The gel section containing radiolabeled C3P bound to His-HNF-4I dimer is shown.

FIG. 3 shows the modulation of HNF-4I transcriptional activity by long chain fatty acyl-CoAs in vitro.

a. Representative experiments showing in vitro transcription of the test template in the presence of increasing concentrations of His-HNF-4I and in the absence (lanes 1–3, 7–9) or presence of 10 µM of added palmitoyl(16:0)-CoA (lanes 4–6) or stearoyl(18:0)-CoA (lanes 10,11) as indicated. Correctly initiated transcripts of the test and control templates are denoted by (→) and (→), respectively.

b. HNF-4I -induced in vitro transcription in the absence (empty bars) or presence of 10 µM each of added palmitoyl (16:0)-CoA (filled bars) or stearoyl(18:0)-CoA (hatched bars). Fold transcription indicates the ratio of specific transcript produced by the test template over transcript from the control template normalized to the ratio observed without HNF-4a. The figure summarizes 5 independent experiments for each acyl-CoA. *-Significant as compared with the respective value in the absence of added ligand.

FIG. 4 shows modulation of HNF-4α activity by long chain fatty acids and xenobiotic amphipathic carboxylates in transient transfection assays.

a. HNF-4I modulation by long chain fatty acids. Fold induction of CAT activity by transfected HNF-4I is determined by evaluating CAT activity in the presence of pSG5-HNF-4I as compared with pSG5 plasmid and as function of respective fatty acids added to the culture medium as indicated. The figure summarizes 3–4 independent experiments for each fatty acid. Mean±S.E.

b. HNF-4I suppression by xenobiotic dicarboxylic acids. Fold induction refers to CAT activity in cells incubated with 3,3,12,12-tetramethyl-tetradecanedioic acid (•), 3,3,14,14-tetramethyl-hexadecanedioic acid (□) and 3,3,16,16-tetramethyl-octadecanedioic acid (▲) proligands normalized to the activity in cells incubated in the absence of added proligands. $EC_{50}$ for the above and other xenobiotic ligands are as follows:

| | |
|---|---|
| 3,3,12,12-tetramethyl-tetradecane dioic acid | >300 µM |
| 3,3,14,14-tetramethyl-hexadecane dioic acid | 155 µM |
| 3,3,16,16-tetramethyl-octadecane dioic acid | 150 µM |
| 2,2,13,13-tetramethyl-tetradecane dioic acid | 230 µM |
| 2,2,15,15-tetramethyl-hexadecane dioic acid | 150 µM |
| 2,2,17,17-tetramethyl-octadecane dioic acid | 150 µM |
| 4,4,13,13-tetramethyl-hexadecane dioic acid | 150 µM |
| 4,4,15,15-tetramethyl-octadecane dioic acid | 150 µM |
| Bezafibrate | 260 µM |
| Nafenopin | 160 µM |
| Indomethacine | 130 µM |

DETAILED DESCRIPTION OF THE INVENTION

Long chain fatty acids are shown here to directly modulated the transcriptional activity of HNF-4α by binding of the respective fatty acyl-CoA thioesters to the HNF-4α ligand binding domain. Transcriptional modulation by HNF-4α agonistic or antagonistic acyl-CoA ligands may result from two apparently independent ligandinduce effects, namely, shifting the HNF-4α oligomeric-dimeric equilibrium or affecting the intrinsic binding affinity of the HNF-4α dimer for its cognate enhancer.

As used herein the following terms have the following meanings:

The term "amphipathic carboxylate" refers to a compound having a hydrophobic backbone and a carboxylic function.

The term "xenobiotic" refers to compounds foreign to the intermediary metabolism of mammals.

The term "Syndrome X" refers to a syndrome comprising of some or all of the following diseases -1) dyslipoproteinemia (combined hypercholesterolemiahypertriglyceridemia, low HDL-cholesterol), 2) obesity (in particular upper body obesity), 3) impaired glucose tolerance (IGT) leading to noninsulin-depedent diabetes mellitus (NIDDM), 4) essential hypertension and (5) thrombogenic/fibrinolytic defects.

The term "modulating" refers to either increasing or decreasing the apparent activity of HNF-4α. The modulation of HNF-4α may be direct, e.g. binding to HNF-4α, or indirect, e.g., mediated by another pathway such as, for example, kinase activity. Compounds of the present invention which bind to HNF-4α may either activate or inhibit its binding to its cognate enhancer as a function of chain length and/or degree of saturation.

Methods of treating Syndrome X are contemplated by the present invention. Such methods include the administration of natural or xenobiotic amphipathic carboxylates. Also contemplated as methods of inhibiting HNF-4α transcriptional activity are suppression by antisense, suppression by antibodies or any other method of reducing the extra activity of HNF-4α.

Methods
HNF-4α Recombinant Proteins

Rat HNF-4α1 cDNA(pLEN4S)[1] was subcloned into the glutathione-S-transferase (GST) encoding pGEX-2T plasmid (Pharmacia) and the resultant plasmid was cleaved with smal and AccI and religated to yield the GST-HNF-4α (LBD) fusion plasmid. The fusion plasmid was expressed in E. coli BL21(DE3) strain by induction with 0.2 mM IPTG for 60 min and the product was purified by affinity chromatography using glutathione-agarose beads (Sigma) to yield the GST-HNF-4α(LBD) fusion protein consisting of amino acids 96-455 of wild type HNF-4α fused to GST. The full length HNF-4α1 cDNA cloned into 6His-pET11d vector was expressed in E. coli. BL21(DE3)plysS.

Ligand Binding Assays

Recombinant GST-HNF-4α(LBD) (100 pmol) or His-HNF-4α (100 pmol) were incubated for 60 min at 22° C. with [$^3$H]palmitoyl(16:0)-CoA (American RadiolabeledChemicals) in 100 µl of 10 mM phosphate buffer (pH 7.4). Competitor ligands or solvent carrier were added as indicated. Free and HNF-4α bound $^3$[H]palmitoyl (16:0)-CoA were separated by Dowex-coated charcoal and bound ligand was quantified by liquid scintillation counting. Nonspecific binding of [$^3$H]palmitoyl(16:0)-CoA was determined by its binding to the GST moiety or to carbonic anhydrase as nonrelevant protein.

Gel Mobility Shift Assays

His-HNF-4α and acyl-CoA (as indicated) were preincubated for 30 min at 22° C. in 11 mM Hepes (pH 7.9) containing 50 mM KCl, 1 mM dithiothreitol, 2.5 mM $MgCl_2$, 10% glycerol, 1 µg of poly(dI-dC) in a final volume of 20 μl. $^{32}$P-labeled oligonucleotide (0.1 ng) consisting of the human C3P apo CIII promoter sequence (−87/−66)$^6$ was then added, and incubation was continued for an additional 15 min. Protein-DNA complexes were resolved by 5% nondenaturing polyacrylamide gel in 0.6×TBE and quantitated by PhosphorImager analysis.

In Vitro Transcription Assays

Reaction mixture contained 20 mM Hepes-KOH (pH 7.9), 5 mM MgCl$_2$, 60 mM KCl, 8% glycerol, 2 mM DTT, 1 mM 3'-0-methyl-GTP, 10 units of T1 RNase, 20 units of RNasin, 0.5 μg sonicated salmon sperm DNA and His-HNF-4α and test ligand as indicated. The mixture was preincubated for 30 min at 22° C. followed by adding 10 ng of pAdML200 control template consisting of the adenovirus major late promoter (−400/+10) linked to a 200 bp G-less cassette and 200 ng of the test template consisting of three C3P copies of the apo CIII promoter sequence (−87/−66) upstream to a synthetic ovalbumin TATA box promoter in front of a 377 bp-G-less cassette. The mixture was further preincubated for 10 min at 22° C. followed by adding 40 μg of HeLa nuclear extract with additional preincubation for 30 min at 30° C. 0.5 mM ATP, 0.5 mM CTP, 25 μM UTP, and 10 μCi of [α-$^{32}$P]UTP (s.a. 800 Ci/mol, Amersham) were then added and the complete reaction mixture was incubated for 45 min at 30° C. in a final volume of 25 μl. The reaction was terminated by adding 175 μl of stop mix (0.1 M sodium acetate (pH 5.2), 10 mM EDTA, 0.1% SDS, 200 μg/ml tRNA) followed by phenol extraction and ethanol precipitation. RNA was resuspended in sample buffer containing 80% formamide and 10 mM Tris-HCl (pH 7.4) and separated on 5% polyacrylamide gel containing 7 M urea in TBE. Correctly initiated transcripts were quantitated by PhosphorImager analysis. The test DNA template was constructed by inserting into PC$_2$AT19 plasmid a PCR-amplified oligonucleotide prepared by using the (C3P)$_3$-TK-CAT plasmid as template and consisting of three copies of the C3P element of the Apo CIII promoter sequence (−87/−66) having an ECoRI and SSTI sites at the 5' and 3' ends, respectively. The resultant plasmid was cleaved with sphl and sacl and ligated to a synthetic oligonucleotide (5'-CGAGGTCCAC-TTCGCTATATATTCCCCGAGCT-3') containing sequences of the HSV thymidine kinase promoter (−41/−29) and of the chicken ovalbumin promoter (−33/−21).

Transfection Assays

COS-7 cells cotransfected for 6 h with the (C3P)$_3$-TK-CAT reporter plasmid (5 μg) and with either the pSG5-HNF-4αexpression plasmid (0.025 μg) or the pSG5 plasmid (0.025 μg) added by calcium phosphate precipitation were cultured in serum free medium with fatty acids (complexed with albumin in a molar ratio of 6:1) added as indicated. β-Galactosidase expression vector pRSGAL (1 μg) added to each precipitate served as an internal control for transfection. The (C3P)$_3$-TK-CAT construct was prepared by inserting a synthetic oligonucleotide encompassing the (−87/−66) Apo CIII promoter sequence (5'-GCAGGTGACCTTTGCCCAGCGCC-3') flanked by HindIII restriction site into pBLCAT2$^{47}$ upstream of the −105 bp thymidine kinase promoter. The construct containing three copies of the synthetic oligonucleotide in the direct orientation was selected and confirmed by sequencing.

Fatty Acyl-CoAs

Fatty acyl-CoAs were prepared by reacting the free acid dissolved in dry acetonitrile with 1,1'-carbonyldiimidazole. The reaction mixture was evaporated to dryness and the respective acyl-imidazole conjugate was reacted with one equivalent of reduced CoA dissolved in 1:1 THF:H$_2$O. Reaction was followed by TLC using silica 60H plates (Merck) (butanol: acetic acid: H$_2$O 5:2:3). The acyl-CoA derivative was precipitated with 0.1 M HCl and the precipitate was washed three times with 0.1 M HCl, three times with peroxide free ether and three times with acetone. The acyl-CoA was spectrophotometrically determined by its 260/232 nm ratio.

EXAMPLES

In order to further illustrate the present invention and advantages therof, the following specific examples are given, it being understood that the same are intended only as illustrative and in nowise limitative.

Example 1

Long Chain Acyl-CoAs are Ligands for HNF-4α

Figure 1A:
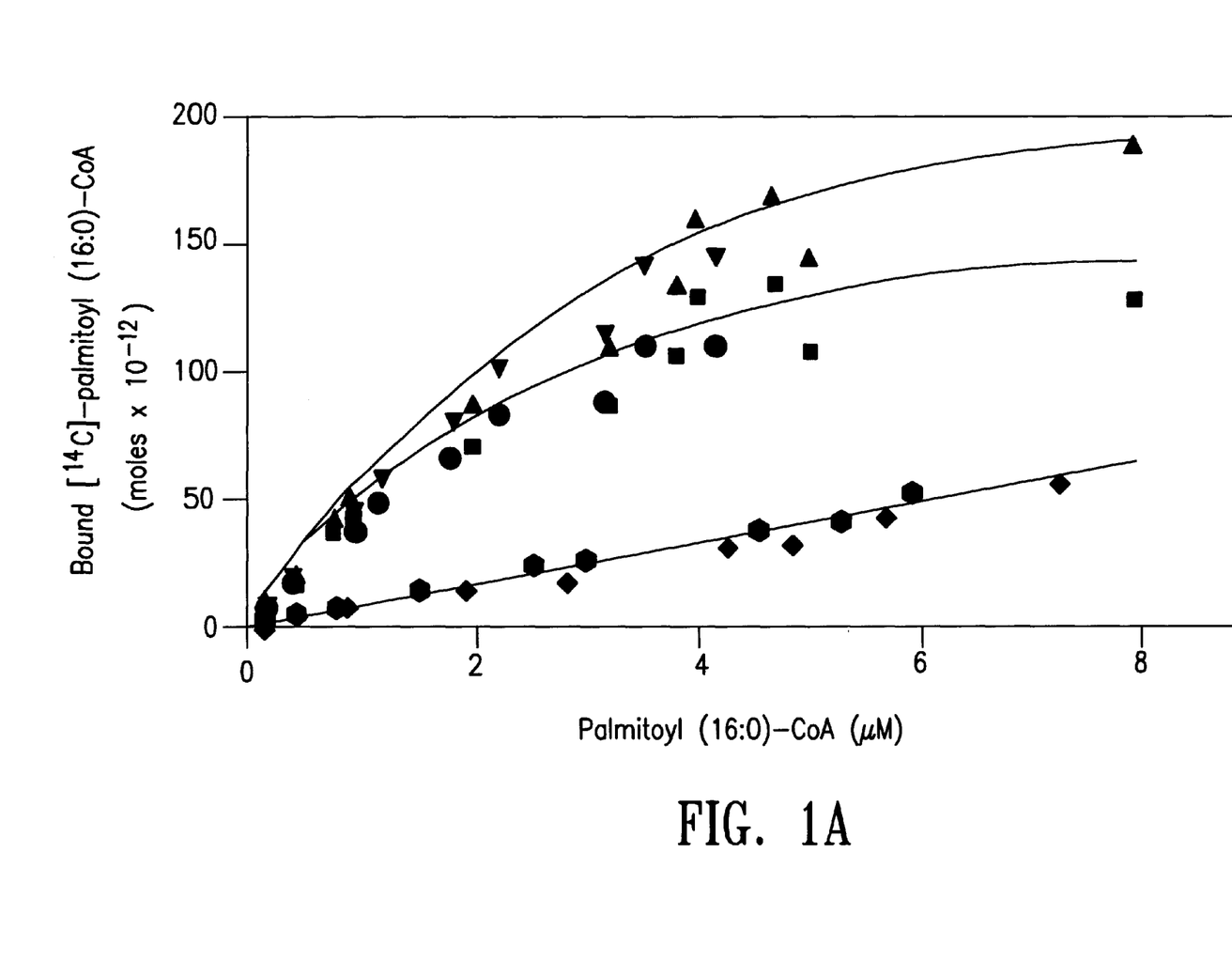
Figure 1B:
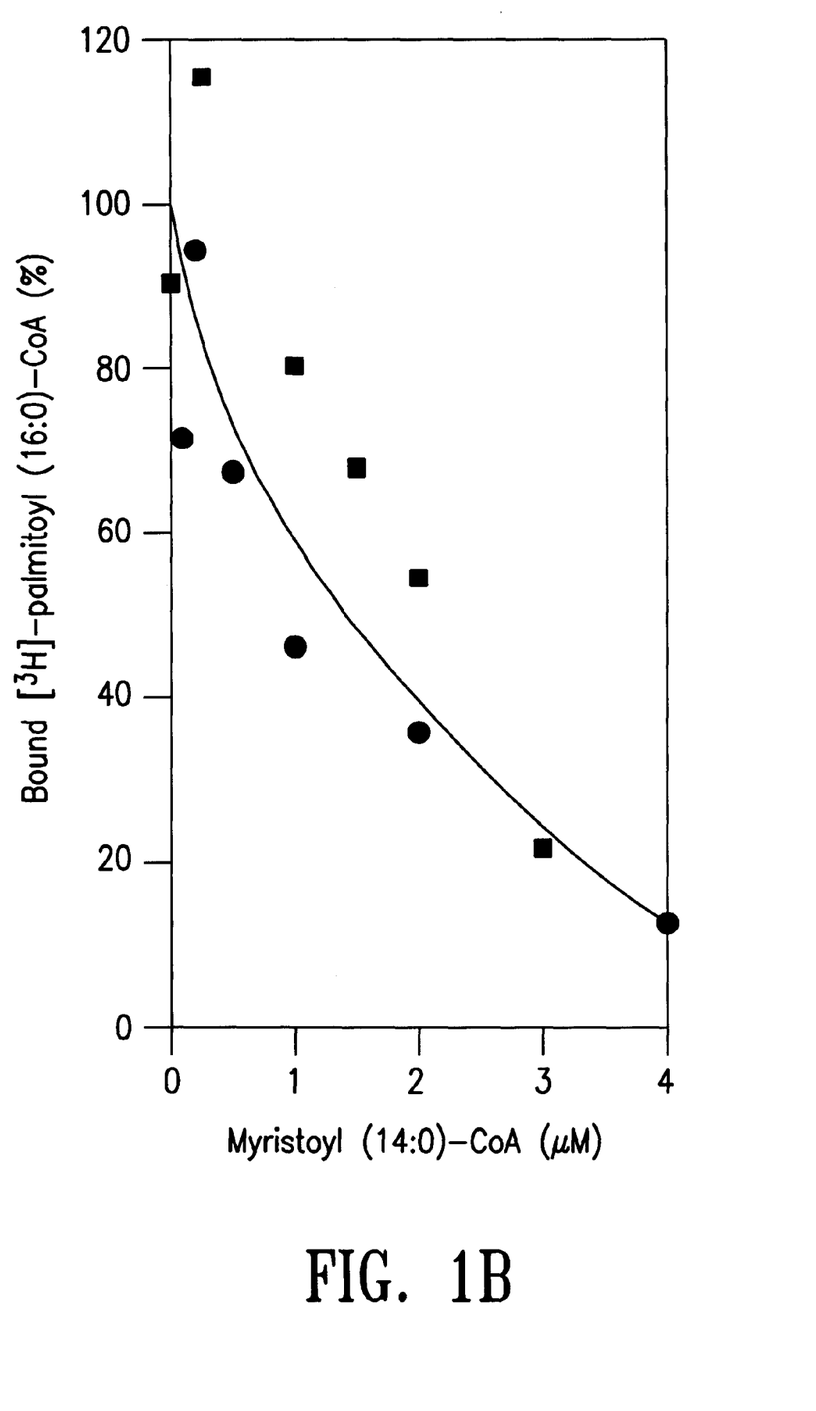

Acyl-CoAs of various chain length and degree of saturation were found to specifically bind to HNF-4α. Binding was exemplified with either the ligand binding domain of HNF-4α fused to glutathione-s-transferase (GST-HNF-4α (LBD)) or the full length HNF-4α protein tagged by 6 histidines (His-HNF-4α). Palmitoyl(16:0)-CoA binding to the ligand binding domain or full length HNF-4α proteins was saturable having a Kd of 2.6 μM and approaching at saturation a ratio of 1 mole of fatty acyl-CoA/mole of HNF-4α (FIG. 1A). Binding was specific for the acyl-CoA whereas the free fatty acid or free CoA were inactive. The binding of acyl-CoAs of variable chain length and degree of saturation was verified by competing with radiolabelled palmitoyl(16:0)-CoA binding to recombinant GST-HNF-4αLBD) or His-HNF-4α (FIG. 1B). Binding was not observed with saturated fatty acyl-CoAs shorter than C12 in chain length. However, the binding affinity of long chain fatty acyl-CoAs for HNF-4α was not substantially affected by chain length or degree of saturation of respective ligands, being in the range of 0.5–3.0 μM. Specificity of binding of long chain fatty acyl-CoAs to HNF-4α was further verified by analyzing the putative binding of palmitoyl(16:0)-CoA to recombinant histidine-tagged peroxisome proliferators activated receptor α (His-PPARα). In contrast to HNF-4α, long chain fatty acyl-CoAs were not bound by PPARα or retinoic acid X receptor α (RXRα). These results indicate that natural long chain fatty acyl-CoAs may bind to the ligand binding domain of HNF-4α and serve as specific ligands of this protein.

Binding of acyl-CoAs to HNF-4α is not limited to natural fatty acyl-CoAs as exemplified above. Thus, binding may be observed with xenobiotic acyl-CoAs (RCOSCoA) where R is a radical consisting of a saturated or unsaturated alkyl chain of 10–24 carbon atoms, one or more of which may be replaced by heteroatom, where one or more of said carbon or heteroatom chain members optionally forming part of a ring, and where said chain being optionally substituted (FIG. 1B).

Example 2

Modulation of HNF-4α Activity by Long Chain Acyl-CoAs

Figure 2A:
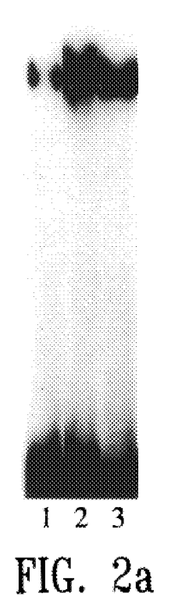
Figure 2B:
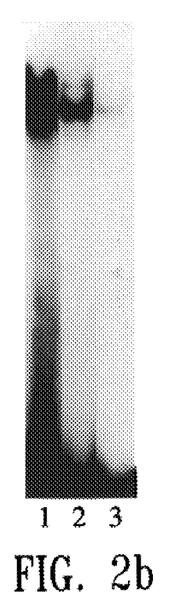
Figure 2C:
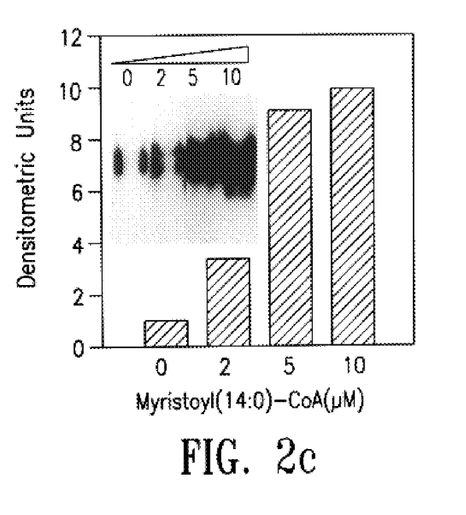

HNF-4α activity as a function of binding of long chain acyl-CoAs was evaluated by studying the binding of HNF-4α to its cognate C3P element of the apo CIII promoter sequence (−87/−66)$^6$ in the presence or absence of added acyl-CoAs of variable chain length, degree of saturation, and degree of substitution. Binding was verified by using a gel mobility shift assay. As shown in FIG. 2, C3P binding to HNF-4α increased with increasing His-HNF-4α concentrations and was activated by natural saturated fatty acyl-CoAs of C12–C16 in chain length. Activation was concentration dependent and maximal in the presence of myristoyl(14:0)-CoA added within a concentration range required for its binding to HNF-4α. Furthermore, some fatty acyl-CoAs as well as xenobiotic acyl-CoAs were found to serve as true antagonists of HNF-4α, namely to inhibit its intrinsic binding to its cognate enhancer. Thus, incubating HNF-4α in the presence of either stearoyl(18:0)-CoA or α-linolenoyl (18:3)-CoA resulted in potent inhibition of its binding to C3P oligo-nucleotide (FIG. 2). Similarly, incubating HNF-4α in the presence of a variety of xenobiotic acyl-CoAs resulted in inhibition of its binding to its cognate C3P oligonucleotide. Hence, natural or xenobiotic acyl-CoAs which bind to HNF-4α may serve as agonists, partial agonists or antagonists of its transcriptional activity as a function of chain length, degree of saturation or degree of substitution.

Figure 3A:
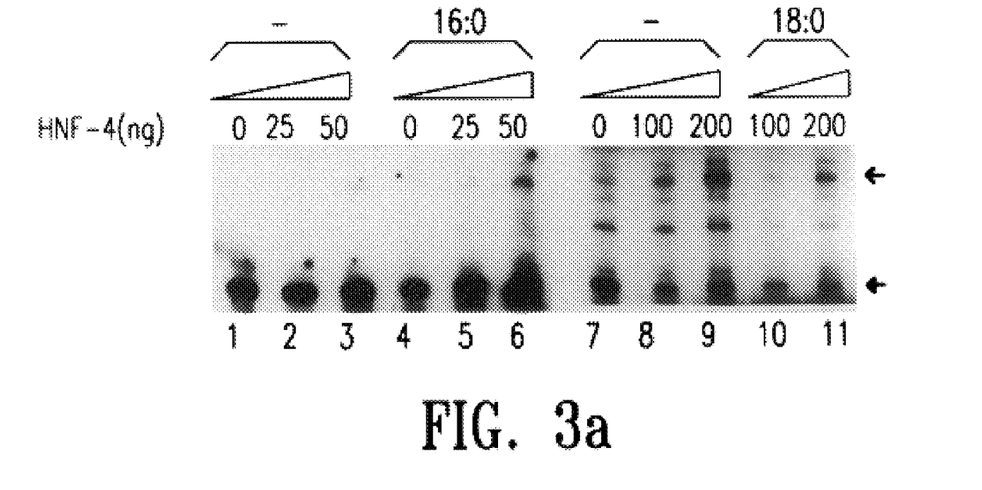
Figure 3B:
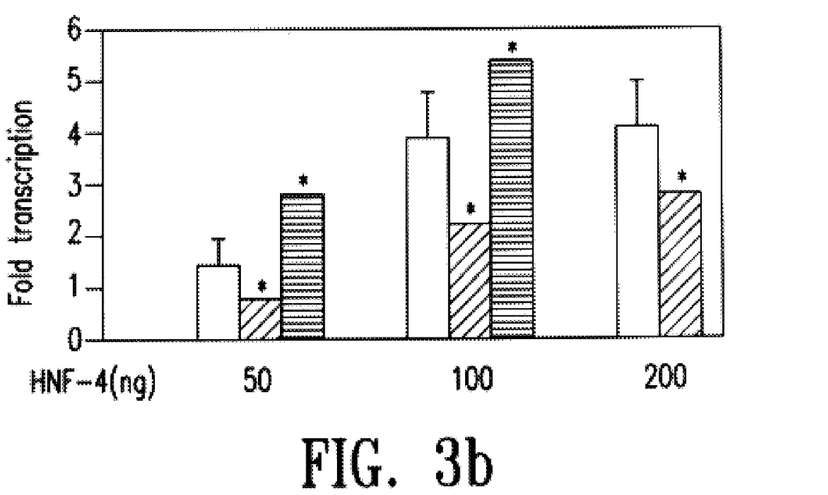

Example 3
Modulation of HNF-4α-induced Transcription by HNF-4α Agonists and Antagonists The effect of agonistic and antagonistic HNF-4α-ligands was further evaluated by analyzing the in vitro transcription rate, catalyzed by added HeLa nuclear extract and induced by recombinant HNF-4α, of a test template consisting of a 377 bp G-less cassette promoted by sequences of the HSV thymidine kinase and chicken ovalbumin promoters and enhanced by three C3P copies of the apo CIII gene promoter. Transcriptional activation by HNF-4α was evaluated in the presence and in the absence of added representative long chain fatty acyl-CoAs. Transcription of a template consisting of a 200 bp G-less cassette driven by the adenovirus major late (AdML) promoter and lacking an HNF-4α enhancer was used as an internal control template. As shown in FIG. 3, in vitro transcription of the test template increased as a function of HNF-4α, approaching saturation at HNF-4α concentrations of 200 ng. HNF-4α induced transcription was activated by added palmitoyl(16:0)-CoA and inhibited by added stearoyl(18:0)-CoA in line with the effect exerted by HNF-4α agonists and antagonists in gel mobility shift assays. Hence, acyl-CoAs which bind to HNF-4α may directly modulate its transcriptional activity in a cell free system.

Figure 4A:
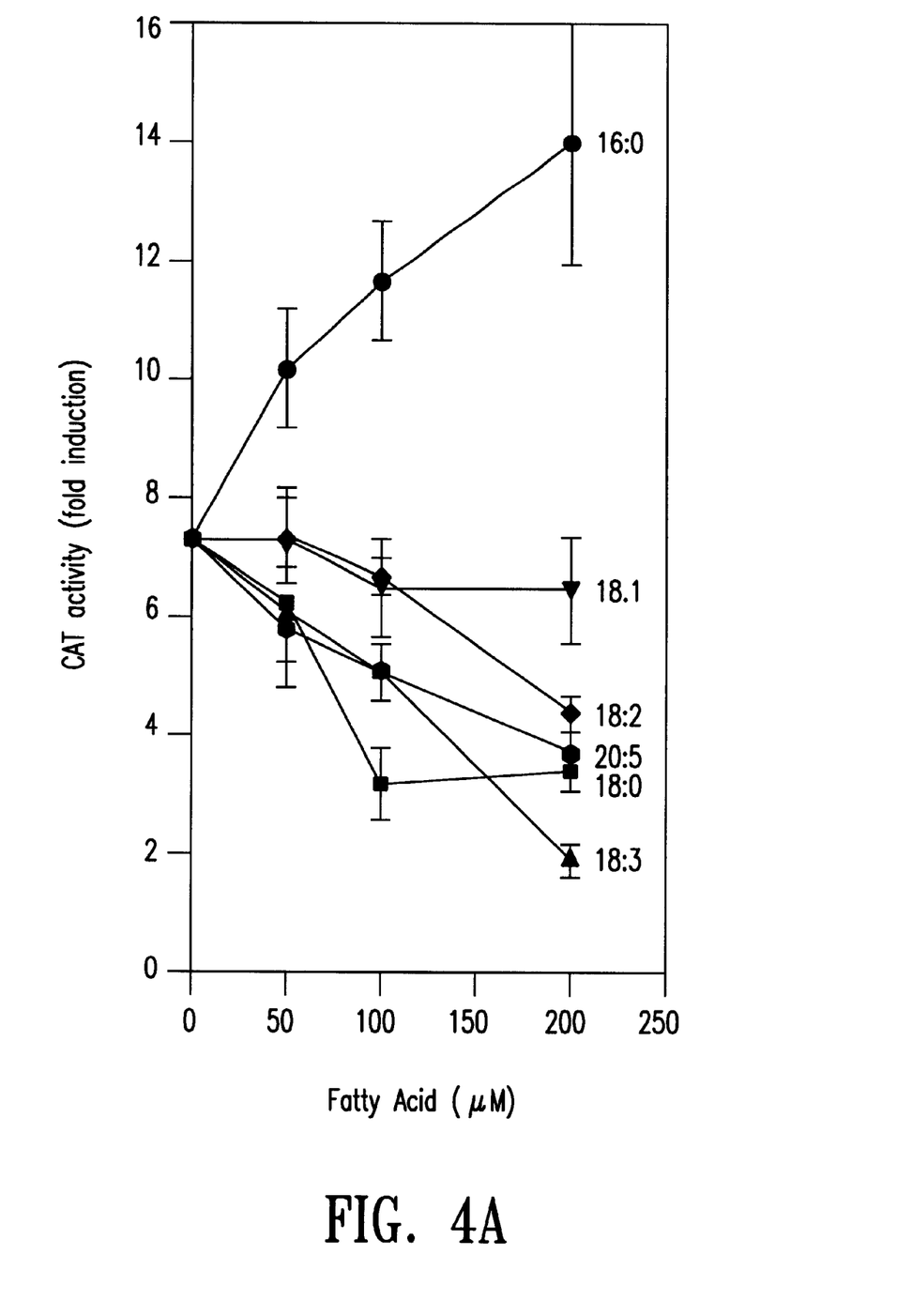
Figure 4B:
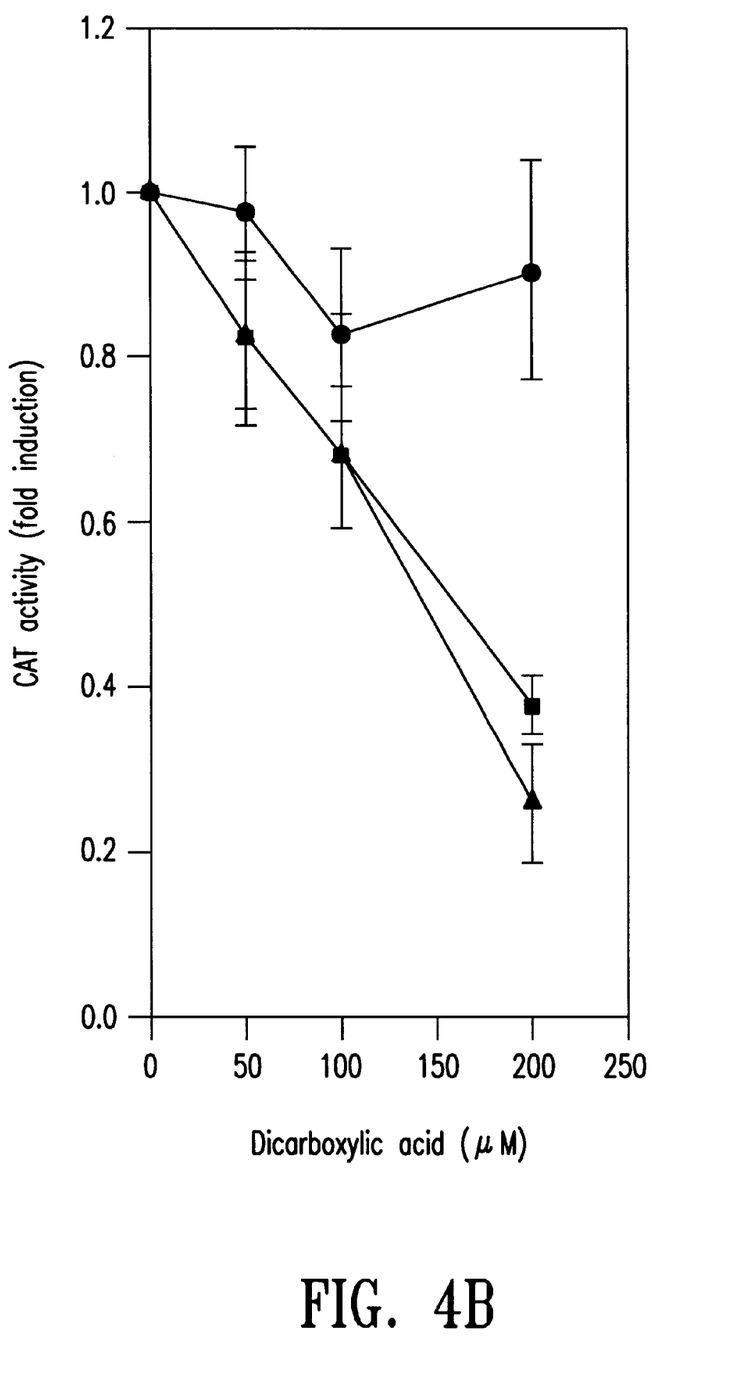

The intracellular effect of HNF-4α ligands on HNF-4α mediated transcription was evaluated in COS-7 cells cotransfected with an expression vector for HNF-4α and with a CAT reporter plasmid driven by a thymidine kinase promoter and enhanced by one to three C3P copies of the apo CIII gene promoter. Transfected cells were incubated in the presence of free fatty acids and xenobiotic amphipathic carboxylates representing agonistic or antagonistic HNF-4α proligands. As shown in FIG. 4a, expression of the C3P-enhanced reporter plasmid was 7 fold activated by HNF-4α in the absence of added fatty acids to the culture medium. Transcriptional activation by transfected HNF-4α could reflect the intrinsic transcriptional activity of the unliganded HNF-4α dimer or could result from binding to HNF-4α of an endogenous activatory acyl-CoA. Adding myristic(14:0) or palmitic(16:0) acid to the culture medium resulted in dose dependent activation of HNF-4α dependent transcription whereas stearic(18:0), α-linolenic(18:3) or eicosapentaenoic (20:5) acids were suppressive in line with the agonistic or antagonistic activities of the respective fatty acyl-CoAs in gel mobility shift assays (FIG. 2) as well as in cell free transcription assays (FIG. 3). Inhibition of HNF-4α transcriptional activity in transfection assays may be similarly observed in the presence of added xenobiotic amphipathic carboxylates (RCOOH) to the culture medium (FIG. 4b) where R is a radical consisting of a saturated or unsaturated alkyl chain of 10–24 carbon atoms, one or more of which may be replaced by heteroatom, where one or more of said carbon or heteroatom chain members optionally forming part of a ring, and where said chain being optionally substituted by hydrocarbyl radical, heterocyclyl radical, lower alkoxy, hydroxyl-substituted lower alkyl, hydroxyl, carboxyl, halogen, phenyl, substituted phenyl, $C_3$–$C_7$ cycloalkyl or substituted $C_3$–$C_7$ cycloalkyl. Hence, intracellular HNF-4α-mediated expression may be modulated by natural long chain fatty acids as well as by xenobiotic amphipathic carboxylates capable of being endogenously converted to their respective CoA thioesters (RCOSCoA). Highly effective inhibitory compounds are the following wherein R is substituted by (ω-carboxyl: 2,2,15,15-tetramethyl-hexadecane-1,16-dioic acid, 2,2,17,17-tetramethyl-octadecane-1,18-dioic acid, 3,3,14,14-tetramethyl-hexadecane-1,16-dioic acid, 3,3,16,16-tetramethyl-octadecane-1,18-dioic acid, 4,4,13,13-tetramethyl-hexadecane-1,16-dioic acid, 4,4,15,15-tetramethyl-octadecane-1,18-dioic acid. Another group of effective compounds is that of compounds wherein R is substituted by ω-hydroxyl: 16-hydroxy-hexadecanoic acid, 18-hydroxy-octadecanoic acid, 16-hydroxy-2,2-dimethyl-hexadecanoic acid, 18-hydroxy-2,2-dimethyl-octadecanoic acid, 16-hydroxy-3,3-dimethyl-hexadecanoic acid, 18-hydroxy-3,3-dimethyl-octa-decanoic acid, 16-hydroxy-4,4-dimethyl-hexadecanoic acid, 18-hydroxy-4,4-dimethyl-octadecanoic acid. Yet another group of somewhat less effective compounds consists of analogues of clofibric acid (fibrate compounds) or nonsteroidal antiinflammatory drugs. The overall effect exerted may reflect the prevailing composition of nuclear acyl-CoAs and the agonistic/antagonistic effect exerted by each when bound to HNF-4α.

Example 4
Physiological Relevance

Inhibition of HNF-4α transcriptional activity by natural or xenobiotic amphipathic carboxylates capable of being endogenously converted to their respective CoA thioesters may offer a therapeutic mode for treating diseases initiated and/or promoted by overexpression of HNF-4α controlled genes. The performance of a concerned amphipathic carboxylate as inhibitor of HNF-4α transcriptional activity will depend in the first place on the intrinsic capacity of its respective CoA thioester to act as HNF-4α antagonist. Presently it is impossible to predict which amphipathic carboxylates capable of being endogenously converted to their respective CoA thioesters may prove as true antagonists of HNF-4α. Thus, myristoyl(14:0)-CoA or palmitoyl (16:0)-CoA proved as activators of HNF-4α transcriptional activity while the next homologue in the series, namely stearoyl(18:0)-CoA proved a true antagonist. It should be pointed out however that partial agonists may induce an apparent inhibition of HNF-4α activity if substituting for endogenous HNF-4α potent agonists or if competing with more productive agonists for binding to HNF-4α.

The overall in vivo performance of an amphipathic carboxylate as an inhibitor of HNF-4α transcriptional activity may not only reflect the intrinsic capacity of its respective CoA thioester to act as HNF-4α antagonist, but will further depend on the specific cell type and the prevailing composition of nuclear fatty acyl-CoAs. This composition may be affected by the dietary/pharmacological availability profile of respective acids, the availability of each for CoA-thioesterification as well as the availability of respective acyl CoAs for hydrolysis by acyl-CoA hydrolases, esterification into lipids, oxidation into products, elongation, desaturation or binding to other acyl-CoA binding proteins. Furthermore, endogenous acyl-CoAs produced by CoA-thioesterification of amphipathic carboxylates other than fatty acids (e.g., retinoic acid, prostaglandins, leukotrienes, others) could bind to HNF-4α and modulate its activity as agonists or antagonists. The resultant effect may further depend on additional nuclear factors which may influence the oligomeric-dimeric equilibrium of HNF-4α, the binding affinity of HNF-4α to its cognate enhancer or the interaction between HNF-4α and proteins of the transcriptional initiation complex. In particular, since HNF-4α and the peroxisomal activators activated receptor (PPAR) share similar DR-1 consensus sequences, and as PPAR may be activated by long chain free fatty acids rather than their respective CoA thioesters, the effect exerted by a certain acyl-CoA and mediated by HNF-4α could be either similar to or antagonized by PPAR activated by the respective free acid.

In spite of the above unknowns, the agonistic/antagonistic profile of acyl-CoA ligands of HNF-4α as exemplified here may help in realizing the molecular basis of effects exerted by dietary fatty acids in vivo and concerned with some of the genes regulated by HNF-4α. Long chain fatty acyl constituents of dietary fat comprise 30–40% of the caloric intake of Western diets. In addition to their substrate role, being mostly oxidized to yield energy or esterified into triglycerides and phospholipids to yield adipose fat and cell membranes, respectively, some dietary fatty acids have long been realized as neutriceutical modulators of the onset and progression of cancer[7], atherogenesis[8], dyslipoproteinemia[9], insulin resistance[10,11], hypertension[12], blood coagulability and fibrinolytic defects[13], inflammatory, immunodeficiency and other diseases. These unexplained effects may now be realized to be accounted for by the effect exerted by the respective acyl-CoAs on HNF-4α transcriptional activity resulting in modulating the expression of genes involved in the onset and progression of the above pathologies. The specific effects exerted by dietary long chain fatty acids on blood lipids and blood coagulation are worth noting in light of the well established effect exerted by HNF-4α on genes coding for proteins involved in lipoproteins metabolism (apolipoproteins AI, AII, B, CIII, microsomal triglyceride transfer protein) and blood coagulation (factors IV, IX, X). Indeed, the well established increase in plasma VLDL-, LDL- and HDL-cholesterol induced by dietary saturated fatty acids of C12–C16 in general and by myristic acid in particular is in line with HNF-4α activation induced by the respective saturated acyl-CoAs and the lack of effect exerted by fatty acyl-CoAs shorter than C12. The surprisingly lowering of blood lipids by the saturated stearic(18:0) acid may be similarly accounted for by the antagonistic effect exerted by stearoyl(18:0)-CoA on HNF-4α activity. Similarly, the lipid lowering effect of mono and polyunsaturated fatty acids, ascribed to substituting for saturated dietary fatty acids[9], is in line with the activity of poly or monounsaturated as compared with saturated fatty acyl-CoAs, being further complemented by the direct inhibition of HNF-4α by linolenoyl(18:3)-CoA, eicosapentaenoyl (20:5)-CoA or docosahexaenoyl(22:6)-CoA. Also, the increase in blood coagulability induced by saturated C12–C16 dietary fatty acids and correlated with a respective increase in factor VII, the decrease in coagulability induced by polyunsaturated dietary fatty acids as well as the surprising decrease in factor VII content and blood coagulability specifically induced by dietary stearic(18:0) acid may be similarly ascribed to the effect exerted by the respective fatty acyl-CoAs on HNF-4α activity resulting in modulating the expression of HNF-4α-controlled genes encoding vitamin K-dependent coagulability factors.

Furthermore, modulation of transcription of HNF-4α-controlled genes by xenobiotic amphipathic carboxylates which may endogenously be esterified to their respective CoA thioesters and act as HNF-4α agonists or antagonists may offer a pharmacological therapeutic mode for diseases initiated or promoted by overexpression of HNF-4α-controlled genes. The examples offered by xenobiotic substituted amphipathic dicarboxylates are worth noting in light of the cumulative information concerned with their pharmacological performance in changing the course of dyslipoproteinemia, obesity, insulin resistance and atherosclerosis in animal models [14-17], namely, of diseases concerned with overexpression of some HNF-4α-controlled genes. The therapeutic efficacy of these drugs may be accounted for by inhibition of HNF-4α transcriptional activity as exemplified here.

What is claimed is:

1. A method of treating an HNF-4 mediated disease state which method comprises administering a therapeutically effective amount of a compound which inhibits HNF-4 controlled transcription independently of PPARα activation.

2. A method of claim 1 wherein said compound comprises an amphipathic carboxylate convertible to its respective CoA thioester.

3. A method of claim 2 wherein said amphipathic carboxylate is a xenobiotic amphipathic carboxylate.

4. A method of claim 2 wherein said amphipathic carboxylate is a C18:3 fatty acid.

5. A method of claim 2 wherein said amphipathic carboxylate is a C20:5 fatty acid.

6. A method of claim 1 wherein said compound shifts the HNF-4 dimer-oligomer equilibrium to favor an oligomer.

7. A method of claim 1 wherein said compound decreases the binding affinity of the HNF-4 dimer for a target gene.

8. A method of claim 1 for the treatment of Syndrome X.

* * * * *

UNITED STATES PATENT AND TRADEMARK OFFICE
CERTIFICATE OF CORRECTION

PATENT NO.   : 6,303,653 B1
DATED        : October 16, 2001
INVENTOR(S)  : Jacob Bar-Tana It is certified that error appears in the above-identified patent and that said Letters Patent is hereby corrected as shown below:

Column 4,
Line 25, change "HNF-4l" to -- HNF-4α. --.
Line 25, change "GST-HNF-4l(LBD)" to -- GST-HNF-4α.(LBD) --.
Line 26, change "HNF-4l(LBD)" to -- HNF-4α.(LBD) --.
Line 27, change "His-HNF-4l" to -- HNF-4α. --.
Line 34, change "HNF-4l" to -- HNF-4α. --.

Column 5,
Line 1, change "His-NHF-4l" to -- His-HNF-4α. --.
Line 4, change "His-NHF-4l" to -- His-HNF-4α. --.
Line 7, change "His-NHF-4l" to -- His-HNF-4α. --.
Line 9, change "His-NHF-4l" to -- His-HNF-4α. --.
Line 11, change "HNF-4l" to -- HNF-4α. --.
Line 15, change "His-HNF-4l" to -- His-HNF-4α. --.
Line 20, change "HNF-4l" to -- HNF-4α. --.
Line 32, change "HNF-4l" to -- HNF-4α. --.
Line 33, change "HNF-4l" to -- HNF-4α. --.
Line 35, change "HNF-4l" to -- HNF-4α. --.
Line 39, change "HNF-4l" to -- HNF-4α. --.

Column 12,
Line 34, before "a therapeutically" insert -- to an individual in need thereof --.

Signed and Sealed this

Eleventh Day of June, 2002

Attest:

Attesting Officer

JAMES E. ROGAN
Director of the United States Patent and Trademark Office